(12) United States Patent
Winsor et al.

(10) Patent No.: US 7,967,797 B2
(45) Date of Patent: Jun. 28, 2011

(54) INTRAVASCULAR VALVE COMPONENT WITH IMPROVED VALVE POSITIONING

(75) Inventors: Chris Winsor, Olathe, KS (US); W. Cary Dikeman, Lenexa, KS (US); Larry C. Smith, Shawnee, KS (US)

(73) Assignee: Nexus Medical, LLC, Lenexa, KS (US)

( * ) Notice: Subject to any disclaimer, the term of this patent is extended or adjusted under 35 U.S.C. 154(b) by 0 days.

(21) Appl. No.: 12/468,650

(22) Filed: May 19, 2009

(65) Prior Publication Data
US 2010/0298782 A1    Nov. 25, 2010

(51) Int. Cl.
*A61M 5/14* (2006.01)
(52) U.S. Cl. ............ 604/256; 604/167.01; 604/167.02; 604/167.03; 604/167.04; 604/237; 604/246; 604/247; 137/846
(58) Field of Classification Search ........... 604/167.01–167.04, 256, 99.03, 604/246–247, 264, 237, 506, 103.06; 137/846
See application file for complete search history.

(56) References Cited

U.S. PATENT DOCUMENTS

| | | |
|---|---|---|
| 274,447 A | 3/1883 | Kennish |
| 1,923,501 A | 8/1933 | Perry |
| 2,524,764 A | 10/1950 | Burke |
| 3,517,682 A | 6/1970 | Smith |
| 4,143,853 A | 3/1979 | Abramson |
| 4,181,145 A | 1/1980 | Mitchell |
| 4,321,923 A | 3/1982 | Nichols |
| 4,341,239 A | 7/1982 | Atkinson |
| 4,434,810 A | 3/1984 | Atkinson |
| 4,451,257 A | 5/1984 | Atchley |
| 4,895,565 A * | 1/1990 | Hillstead ............ 604/167.04 |
| 4,995,863 A | 2/1991 | Nichols et al. |
| D320,082 S | 9/1991 | Wyatt et al. |
| D323,709 S | 2/1992 | Wyatt et al. |
| D323,889 S | 2/1992 | Wyatt et al. |
| 5,147,313 A | 9/1992 | Dikeman |
| 5,147,332 A | 9/1992 | Moorehead |
| 5,152,753 A | 10/1992 | Laguette et al. |
| 5,160,325 A | 11/1992 | Nichols et al. |

(Continued)

FOREIGN PATENT DOCUMENTS
EP    0416467 A2    3/1991
(Continued)

OTHER PUBLICATIONS

Restriction Requirement dated May 3, 2007, in U.S. Appl. No. 10/304,833, filed Nov. 26, 2002 now US 7601141; Issued Oct. 13, 2009. pp. 1-5.*

(Continued)

*Primary Examiner* — Kevin C Sirmons
*Assistant Examiner* — Edelmira Bosques
(74) *Attorney, Agent, or Firm* — Hovey Williams LLP

(57) ABSTRACT

An intravascular valve component broadly includes a valve case and a flexible pressure-actuated flow control valve. The valve case includes attached proximal and distal case portions that present respective spaced apart fluid ports and a fluid passageway extending between the ports. The flexible pressure-actuated flow control valve is disposed within the fluid passageway and includes a slitted central valve wall and an annular flange surrounding the central valve wall. The annular flange includes a radially-extending flange wall and a projection extending axially from the flange wall, with the projection engaging one of the case portions to restrict radial movement of the flow control valve relative to the valve case.

9 Claims, 6 Drawing Sheets

U.S. PATENT DOCUMENTS

| | | | |
|---|---|---|---|
| 5,169,393 | A | 12/1992 | Moorehead et al. |
| 5,201,722 | A | 4/1993 | Moorehead et al. |
| 5,205,834 | A | 4/1993 | Moorehead et al. |
| 5,249,598 | A | 10/1993 | Schmidt |
| 5,251,873 | A | 10/1993 | Atkinson et al. |
| 5,295,657 | A | 3/1994 | Atkinson |
| 5,295,658 | A | 3/1994 | Atkinson et al. |
| 5,356,396 | A | 10/1994 | Wyatt et al. |
| 5,360,413 | A | 11/1994 | Leason et al. |
| 5,389,091 | A | 2/1995 | Moorehead |
| 5,402,982 | A | 4/1995 | Atkinson et al. |
| 5,409,471 | A | 4/1995 | Atkinson et al. |
| 5,431,202 | A | 7/1995 | Dikeman et al. |
| 5,501,426 | A | 3/1996 | Atkinson et al. |
| 5,533,708 | A | 7/1996 | Atkinson et al. |
| 5,603,706 | A | 2/1997 | Wyatt et al. |
| 5,632,735 | A | 5/1997 | Wyatt et al. |
| 5,752,938 | A * | 5/1998 | Flatland et al. ........... 604/167.01 |
| 5,843,044 | A | 12/1998 | Moorehead |
| 6,024,729 | A | 2/2000 | Dehdashtian et al. |
| 6,270,489 | B1 | 8/2001 | Wise et al. |
| 6,364,867 | B2 | 4/2002 | Wise et al. |
| 7,169,130 | B2 * | 1/2007 | Exline et al. ............. 604/167.01 |
| 7,601,141 | B2 | 10/2009 | Dikeman et al. |
| 2001/0041872 | A1 * | 11/2001 | Paul, Jr. ................... 604/167.04 |
| 2002/0165492 | A1 | 11/2002 | Davey et al. |
| 2004/0102738 | A1 * | 5/2004 | Dikeman et al. .............. 604/256 |
| 2004/0147871 | A1 | 7/2004 | Burnett |
| 2005/0010176 | A1 | 1/2005 | Dikeman et al. |
| 2007/0225648 | A1 * | 9/2007 | Winsor et al. ............ 604/167.04 |
| 2008/0086095 | A1 | 4/2008 | Dikeman et al. |
| 2009/0264832 | A1 | 10/2009 | Dikeman et al. |
| 2010/0036328 | A1 | 2/2010 | Dikeman et al. |

FOREIGN PATENT DOCUMENTS

FR                 2707505 A1     1/1995

OTHER PUBLICATIONS

Amendment Dated Dec. 21, 2007, in U.S. Appl. No. 10/304,833, filed Nov. 26, 2002 now US 7601141; Issued Oct. 13, 2009. pp. 1-16.*
Printout from website for Vernay Laboratories, Inc. (www.vernay.com) depicting prior art bi-directional valve designated Part No. VL2959-101 (printed Feb. 2, 2007).
European Communication dated Sep. 10, 2007 from European Application No. 03029630.5, filed Dec. 22, 2003.
European Communication dated Jan. 29, 2007 from European Application No. 03029630.5, filed Dec. 22, 2003.
European Communication dated May 26, 2004 from European Application No. 03029630.5, filed Dec. 22, 2003.
European Communication dated Oct. 12, 2007 from European Application No. 07016563.4, filed Aug. 23, 2007.
English Translation of French Patent No. FR2707505, published Jan. 20, 1995, translation dated Nov. 2, 2007.
European Communication dated Oct. 16, 2007 from European Application No. 07016562.6, filed Sep. 28, 2007.
Reply dated Aug. 3, 2007, from European Application No. 03029630.5, filed Dec. 22, 2003; now European Patent No. 1547646, Issued: Oct. 8, 2008.
Reply dated Jan. 10, 2008, from European Application No. 03029630.5, filed Dec. 22, 2003; now European Patent No. 1547646, Issued: Oct. 8, 2008.
European Communication dated Apr. 25, 2008, regarding Intent to Grant, from European Application No. 03029630.5, filed Dec. 22, 2003; now European Patent No. 1547646, Issued: Oct. 8, 2008.
Decision to Grant European Patent dated Sep. 11, 2008, from European Application No. 03029630.5, filed Dec. 22, 2003; now European Patent No. 1547646, Issued: Oct. 8, 2008.
Non-final Office Action dated Apr. 12, 2010, in U.S. Appl. No. 12/492,370, filed Jun. 26, 2009.
Amendment dated Jul. 12, 2010, in U.S. Appl. No. 12/492,370, filed Jun. 26, 2009.
Applicant's Interview Summary dated Aug. 3, 2010, in U.S. Appl. No. 12/492,370, filed Jun. 26, 2009.
Restriction Requirement dated Sep. 20, 2004, in U.S. Appl. No. 10/304,833, filed Nov. 26, 2002; now U.S. Patent No. 7,601,141, Issued: Oct. 13, 2009.
Response to Restriction Requirement dated Oct. 19, 2004, in U.S. Appl. No. 10/304,833, filed Nov. 26, 2002; now U.S. Patent No. 7,601,141, Issued: Oct. 13, 2009.
Non-final Office Action dated Jan. 7, 2005, in U.S. Appl. No. 10/304,833, filed Nov. 26, 2002; now U.S. Patent No. 7,601,141, Issued: Oct. 13, 2009.
Amendment dated Jun. 7, 2005, in U.S. Appl. No. 10/304,833, filed Nov. 26, 2002; now U.S. Patent No. 7,601,141, Issued: Oct. 13, 2009.
Final Office Action dated Aug. 25, 2005, in U.S. Appl. No. 10/304,833, filed Nov. 26, 2002; now U.S. Patent No. 7,601,141, Issued: Oct. 13, 2009.
Amendment dated Nov. 18, 2005, in U.S. Appl. No. 10/304,833, filed Nov. 26, 2002; now U.S. Patent No. 7,601,141, Issued: Oct. 13, 2009.
Non-Final Office Action dated Dec. 13, 2005, in U.S. Appl. No. 10/304,833, filed Nov. 26, 2002; now U.S. Patent No, 7,601,141, Issued: Oct. 13, 2009.
Amendment dated Mar. 13, 2006, in U.S. Appl. No. 10/304,833, filed Nov. 26, 2002; now U.S. Patent No. 7,601,141, Issued: Oct. 13, 2009.
Final Office Action dated Jun. 6, 2006, in U.S. Appl. No. 10/304,833, filed Nov. 26, 2002; now U.S. Patent No. 7,601,141, Issued: Oct. 13, 2009.
Amendment dated Aug. 30, 2006, in U.S. Appl. No. 10/304,833, filed Nov. 26, 2002; now U.S. Patent No. 7,601,141, Issued: Oct. 13, 2009.
Examiner's Interview Summary dated Sep. 5, 2006, in U.S. Appl. No. 10/304,833, filed Nov. 26, 2002; now U.S. Patent No. 7,601,141, Issued: Oct. 13, 2009.
Non-Final Office Action dated Oct. 19, 2006, in U.S. Appl. No. 10/304,833, filed Nov. 26, 2002; now U.S. Patent No. 7,601,141, Issued: Oct. 13, 2009.
Amendment dated Feb. 20, 2007, in U.S. Appl. No. 10/304,833, filed Nov. 26, 2002; now U.S. Patent No. 7,601,141, Issued: Oct. 13, 2009.
Restriction Requirement dated May 3, 2007, in U.S. Appl. No. 10/304,833, filed Nov. 26, 2002; now U.S. Patent No. 7,601,141, Issued: Oct. 13, 2009.
Response to Restriction Requirement dated Jul. 3, 2007, in U.S. Appl. No. 10/304,833, filed Nov. 26, 2002; now U.S. Patent No. 7,601,141, Issued: Oct. 13, 2009.
Notice of Allowance dated Sep. 11, 2007, in U.S. Appl. No. 10/304,833, filed Nov. 26, 2002; now U.S. Patent No. 7,601,141, Issued: Oct. 13, 2009.
Request for Continued Examination dated Dec. 11, 2007, in U.S. Appl. No. 10/304,833, filed Nov. 26, 2002; now U.S. Patent No. 7,601,141, Issued: Oct. 13, 2009.
Amendment dated Dec. 21, 2007, in U.S. Appl. No. 10/304,833, filed Nov. 26, 2002; now U.S. Patent No. 7,601,141, Issued: Oct. 13, 2009.
Non-final Office Action dated Mar. 17, 2008, in U.S. Appl. No. 10/304,833, filed Nov. 26, 2002; now U.S. Patent No. 7,601,141, Issued: Oct. 13, 2009.
Amendment dated Aug. 15, 2008, in U.S. Appl. No. 10/304,833, filed Nov. 26, 2002; now U.S. Patent No. 7,601,141, Issued: Oct. 13, 2009.
Examiner Interview Summary dated Aug. 21, 2008, in U.S. Appl. No. 10/304,833, filed Nov. 26, 2002; now U.S. Patent No. 7,601,141, Issued: Oct. 13, 2009.
Notice of Allowance dated Nov. 20, 2008, in U.S. Appl. No. 10/304,833, filed Nov. 26, 2002; now U.S. Patent No. 7,601,141, Issued: Oct. 13, 2009.
Issue Fee Payment dated Feb. 20, 2009, in U.S. Appl. No. 10/304,833, filed Nov. 26, 2002; now U.S. Patent No. 7,601,141, Issued: Oct. 13, 2009.
Notice of Allowance dated Sep. 9, 2009, in U.S. Appl. No. 10/304,833, filed Nov. 26, 2002; now U.S. Patent No. 7,601,141, Issued: Oct. 13, 2009.
Issue Notification dated Sep. 23, 2009, in U.S. Appl. No. 10/304,833, filed Nov. 26, 2002; now U.S. Patent No. 7,601,141, Issued: Oct. 13, 2009.
Non-final Office Action dated Jun. 24, 2010, in U.S. Appl. No. 12/577,632, filed Oct. 12, 2009.
Office Action dated Feb. 11, 2010, in Canadian Patent Application No. 2,452,309; Filed: Dec. 8, 2003.

European Communication dated Jun. 6, 2008, from European Application No. 07016563.4, filed Aug. 23, 2007; now European Patent No. 1854502, Issued: Mar. 3, 2010.
Reply dated Dec. 8, 2008, from European Application No. 07016563.4, filed Aug. 23, 2007; now European Patent No. 1854502, Issued: Mar. 3, 2010.
European Communication dated Feb. 13, 2009, from European Application No. 07016563.4, filed Aug. 23, 2007; now European Patent No. 1854502, Issued: Mar. 3, 2010.
Reply dated Aug. 4, 2009, from European Application No. 07016563.4, filed Aug. 23, 2007; now European Patent No. 1854502, Issued: Mar. 3, 2010.
European Communication dated Sep. 17, 2009, regarding Intent to Grant, from European Application No. 07016563.4, filed Aug. 23, 2007; now European Patent No. 1854502, Issued: Mar. 3, 2010.
Decision to Grant European Patent dated Feb. 4, 2010, from European Application No. 07016563.4, filed Aug. 23, 2007; now European Patent No. 1854502, Issued: Mar. 3, 2010.
European Communication dated Jun. 19, 2008, from European Application No. 07016562.6, filed Sep. 28, 2007; now European Patent No. 1857137; Issued: Feb. 24, 2010.

Reply dated Dec. 18, 2008, from European Application No. 07016562.6, filed Sep. 28, 2007; now European Patent No. 1857137; Issued: Feb. 24, 2010.
European Communication dated Feb. 13, 2009, from European Application No. 07016562.6, filed Sep. 28, 2007; now European Patent No. 1857137; Issued: Feb. 24, 2010.
Reply dated Aug. 10, 2009, from European Application No. 07016562.6, filed Sep. 28, 2007; now European Patent No. 1857137; Issued: Feb. 24, 2010.
European Communication dated Sep. 21, 2009, regarding Intent to Grant, from European Application No. 07016562.6, filed Sep. 28, 2007; now European Patent No. 1857137; Issued: Feb. 24, 2010.
Decision to Grant European Patent dated Jan. 28, 2010, from European Application No. 07016562.6, filed Sep. 28, 2007; now European Patent No. 1857137; Issued: Feb. 24, 2010.
Notification of Transmittal of the International Search Report and The Written Opinion of the International Searching Authority, or the Declaration dated Jan. 5, 2011; International Application No. PCT/US2010/033548; International Filing Date: May 4, 2010; Applicant: Nexus Medical, LLC.

* cited by examiner

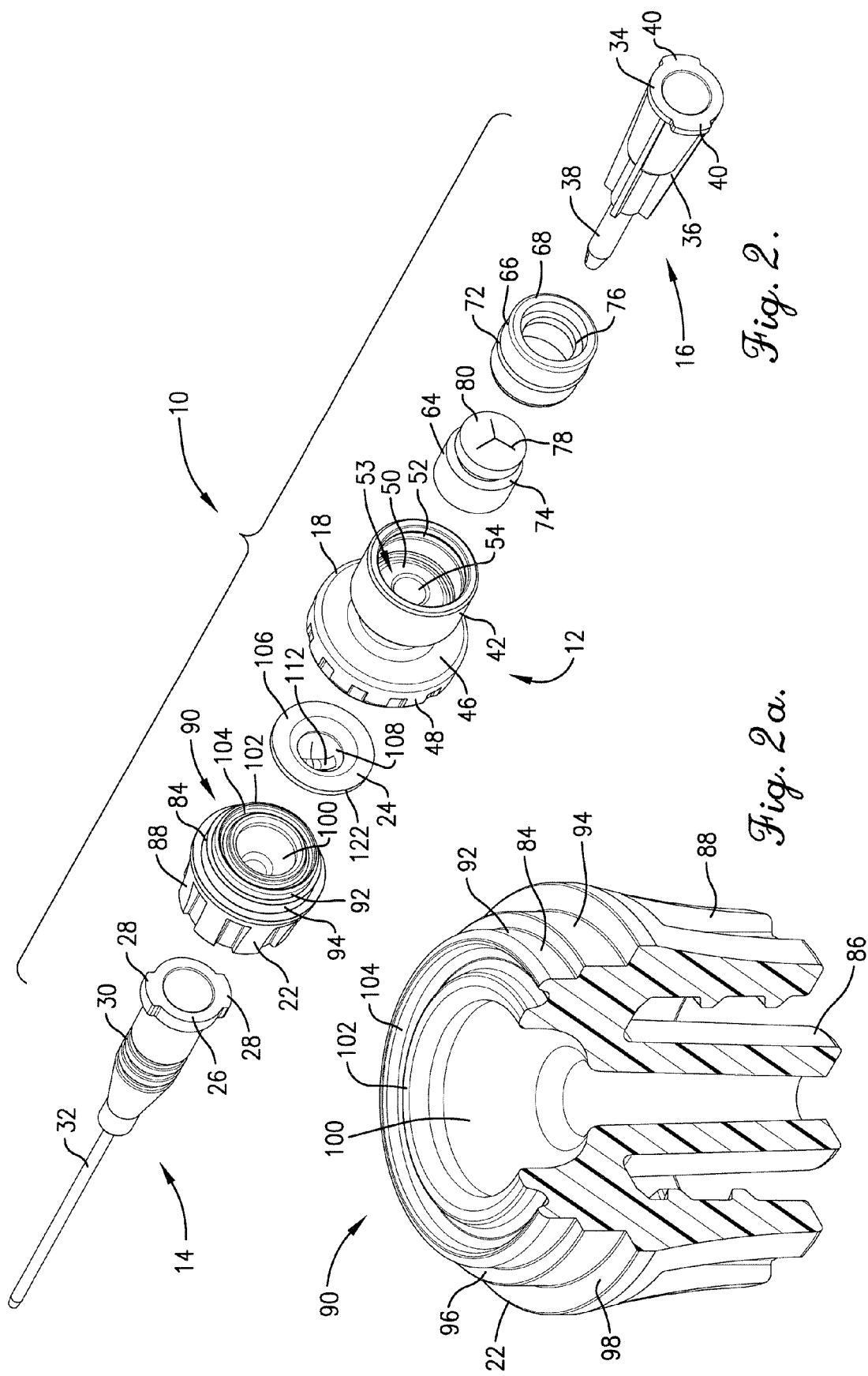

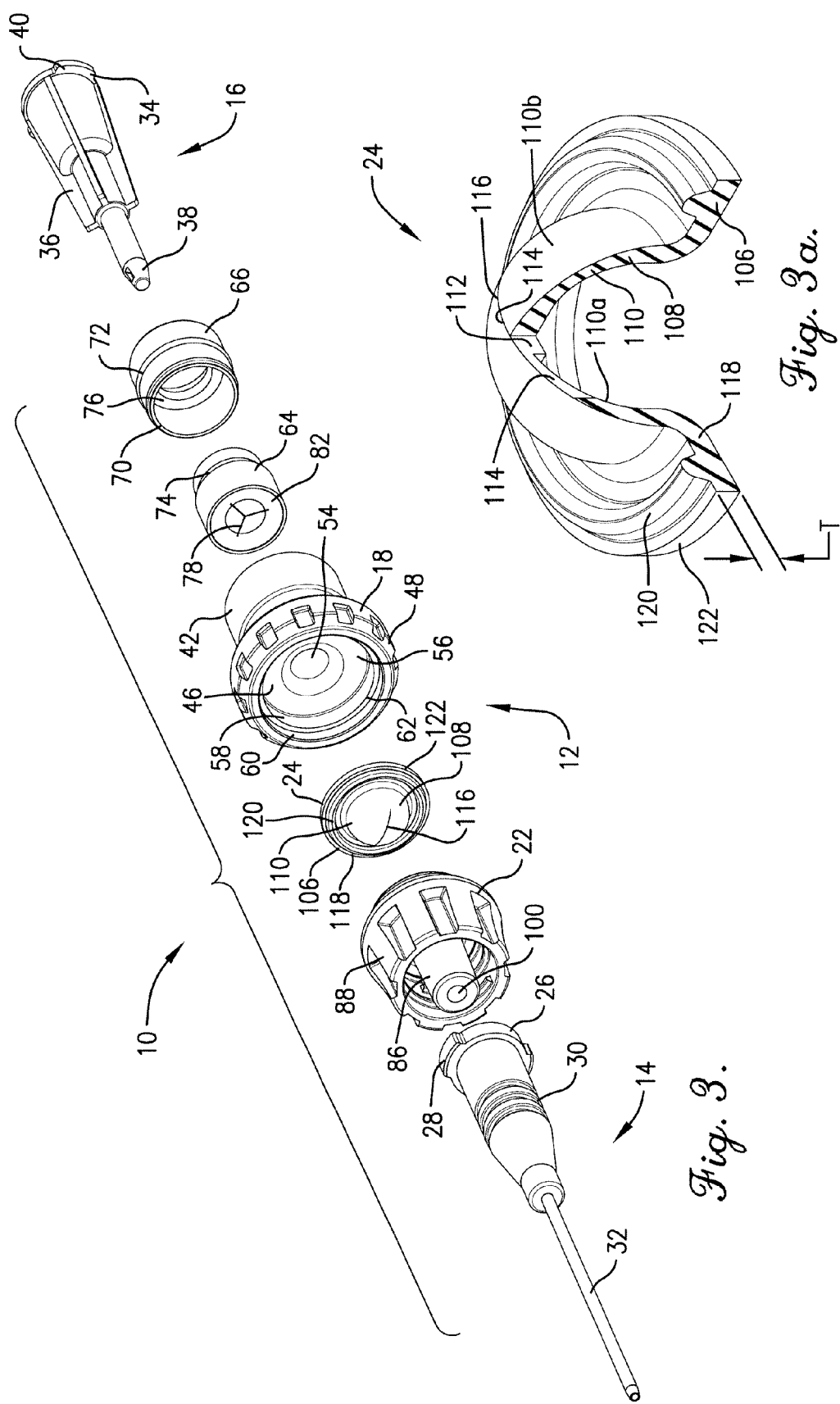

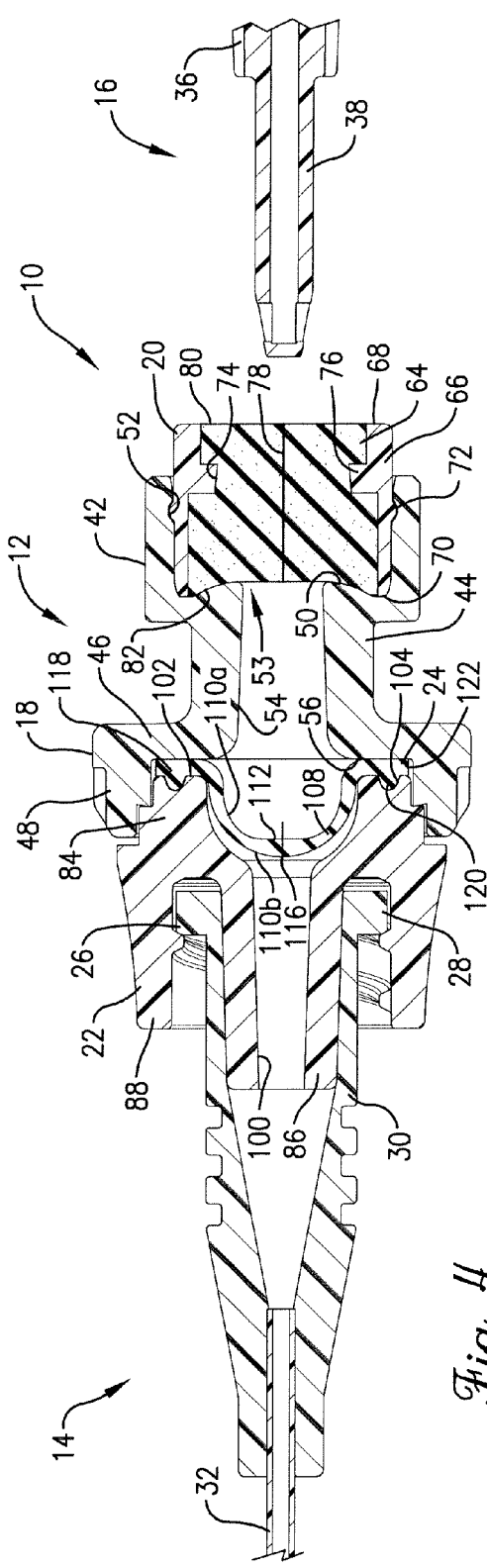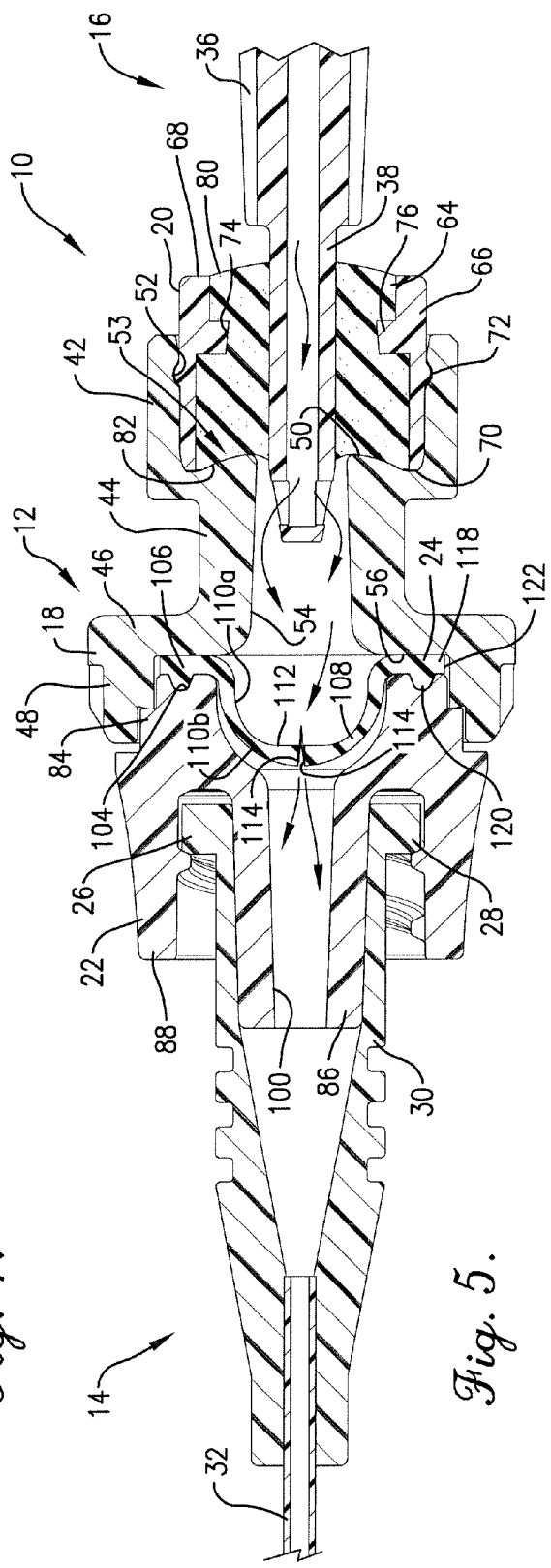

INTRAVASCULAR VALVE COMPONENT WITH IMPROVED VALVE POSITIONING

BACKGROUND

1. Field

The present invention relates generally to infusion devices used for the administration of various fluids to patients. More specifically, embodiments of the present invention concern an intravascular valve component for a catheter.

2. Discussion of Prior Art

The use of intravenous devices for the administration of parenteral and other fluids to patients is a common practice. A variety of devices for such purposes have been proposed in the past, such as a simple length of tubing having a fitting on one end for making connection with a source of fluid (e.g., a bottle or flexible bag), while the other end is provided with a needle or catheter which may be inserted into the vein of a patient. A persistent problem with prior infusion devices is referred to as blood reflux, or the tendency for small amounts of blood from the patient to be drawn into the infusion apparatus. Blood reflux can occur in prior art devices, for example, when a gravity supply fluid source is empty or when a cannula is removed from a septum or port.

Prior art pressure-activated infusion devices that reduce blood reflux using a flexible check valve are problematic due to manufacturing-related issues. Flexible check valves are notoriously difficult to align relative to the internal passage of the valve housing. Off-axis misalignment of the check valve can cause the valve to inadvertently or prematurely open. Furthermore, prior art check valves are also known to shift or "squirm" within the housing, often when the valves are seated and secured in the housing. This inadvertent movement can also cause valve misalignment and improper operation.

There is accordingly a need in the art for improved intravascular devices equipped with a valve component that eliminates the possibility of blood reflux and can be reliably manufactured.

SUMMARY

Embodiments of the present invention provide an intravascular valve component that does not suffer from the problems and limitations of the prior art devices set forth above.

A first aspect of the present invention concerns an intravascular valve component that broadly includes a valve case and a flexible pressure-actuated flow control valve. The valve case includes attached proximal and distal case portions. The case portions present respective spaced apart fluid ports and a fluid passageway extending between the ports. The flexible pressure-actuated flow control valve is disposed along the fluid passageway to control fluid flow therethrough. The valve includes a slit central valve wall and an annular flange surrounding the central valve wall. The annular flange includes a radially-extending flange wall and a projection extending axially from the flange wall. One of the case portions presents an opening that receives the projection therein. The flange wall is engagingly received between the attached case portions, with the projection engaging the one of the case portions to restrict radial movement of the flow control valve relative to the valve case.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 2 is an exploded proximal perspective view of the catheter assembly shown in FIG. 1, particularly showing a luer lock fitting, a septum support body, a split septum unit, and a flow control valve of the injection site;

FIG. 2a is an enlarged perspective view of the luer lock fitting shown in FIGS. 1 and 2, showing the fitting cross-sectioned to depict a grooved valve seat, a male end extending distally from the valve seat, and a connector wall extending distally from the valve seat and surrounding the male end;

FIG. 3 is an exploded distal perspective view of the catheter assembly shown in FIGS. 1 and 2;

FIG. 3a is a distal perspective of the flow control valve shown in FIGS. 2 and 3, showing the flow control valve cross-sectioned to depict a slit central valve wall and an annular flange surrounding the central valve wall, and further showing a radially-extending wall of the flange and an endless annular projection extending distally from the flange wall;

FIG. 4 is a cross section of the catheter assembly shown in FIGS. 1, 2, and 3, showing the peripheral catheter connected to the luer lock fitting and the cannula removed from the split septum unit, and further showing the slit central valve wall in a closed configuration to prevent infusion and aspiration fluid flow;

Figure 6:
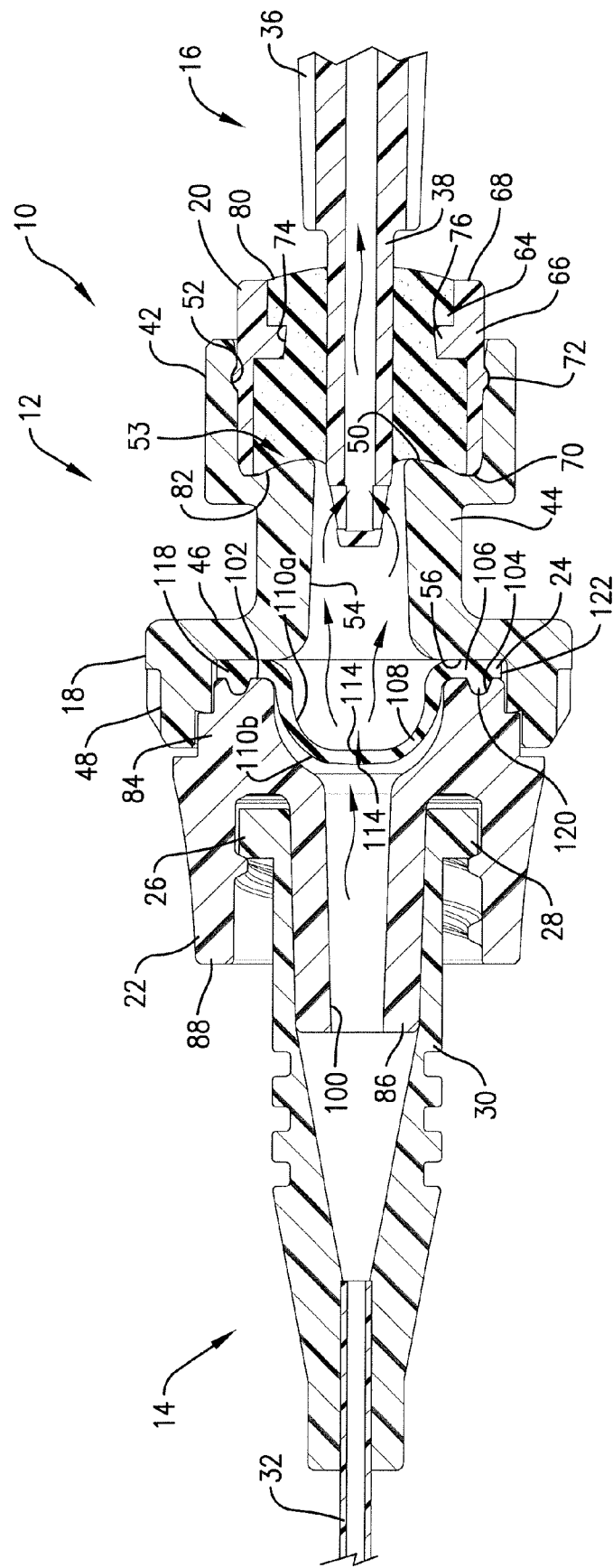
Figure 7:
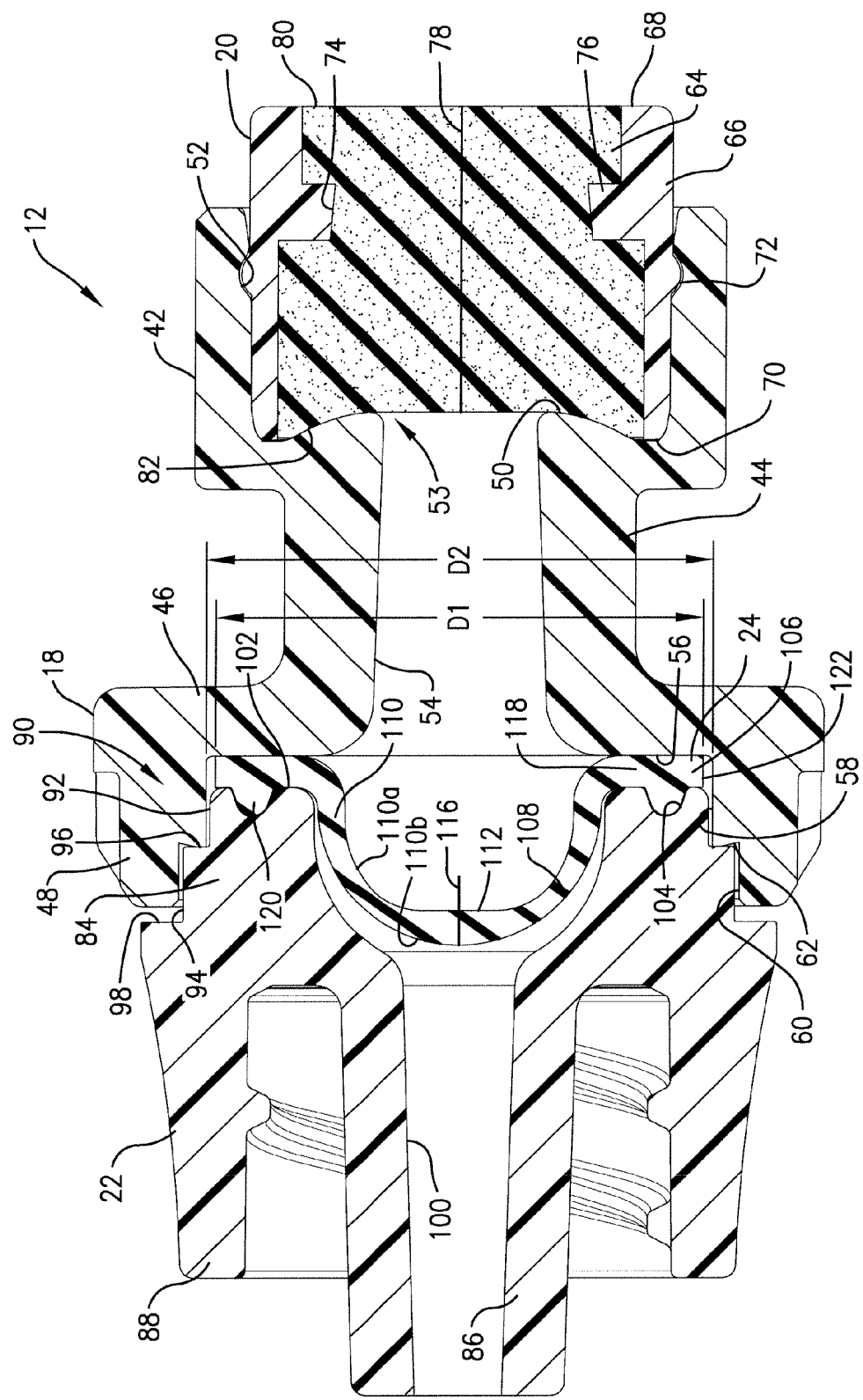

FIG. 5 is a cross section of the catheter assembly shown in FIGS. 1, 2, 3, and 4, showing the cannula inserted into the split septum unit and providing infusion flow through the internal passageway presented by the injection site, with the slit central valve wall in an open infusion configuration where internal opposed edges of the valve wall are shifted distally and away from each other to allow infusion fluid flow through the valve;

FIG. 6 is a cross section of the catheter assembly shown in FIGS. 1, 2, 3, 4, and 5, showing the cannula inserted into the split septum unit and receiving aspiration flow from the internal passageway, with the slit central valve wall in an open aspiration configuration where the internal opposed edges are shifted proximally and away from each other to allow aspiration fluid flow through the valve; and FIG. 7 is an enlarged cross section of the intravascular injection site shown in FIGS. 1, 2, 3, 4, 5, and 6, showing the slit central valve wall in the closed configuration.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Figure 1:
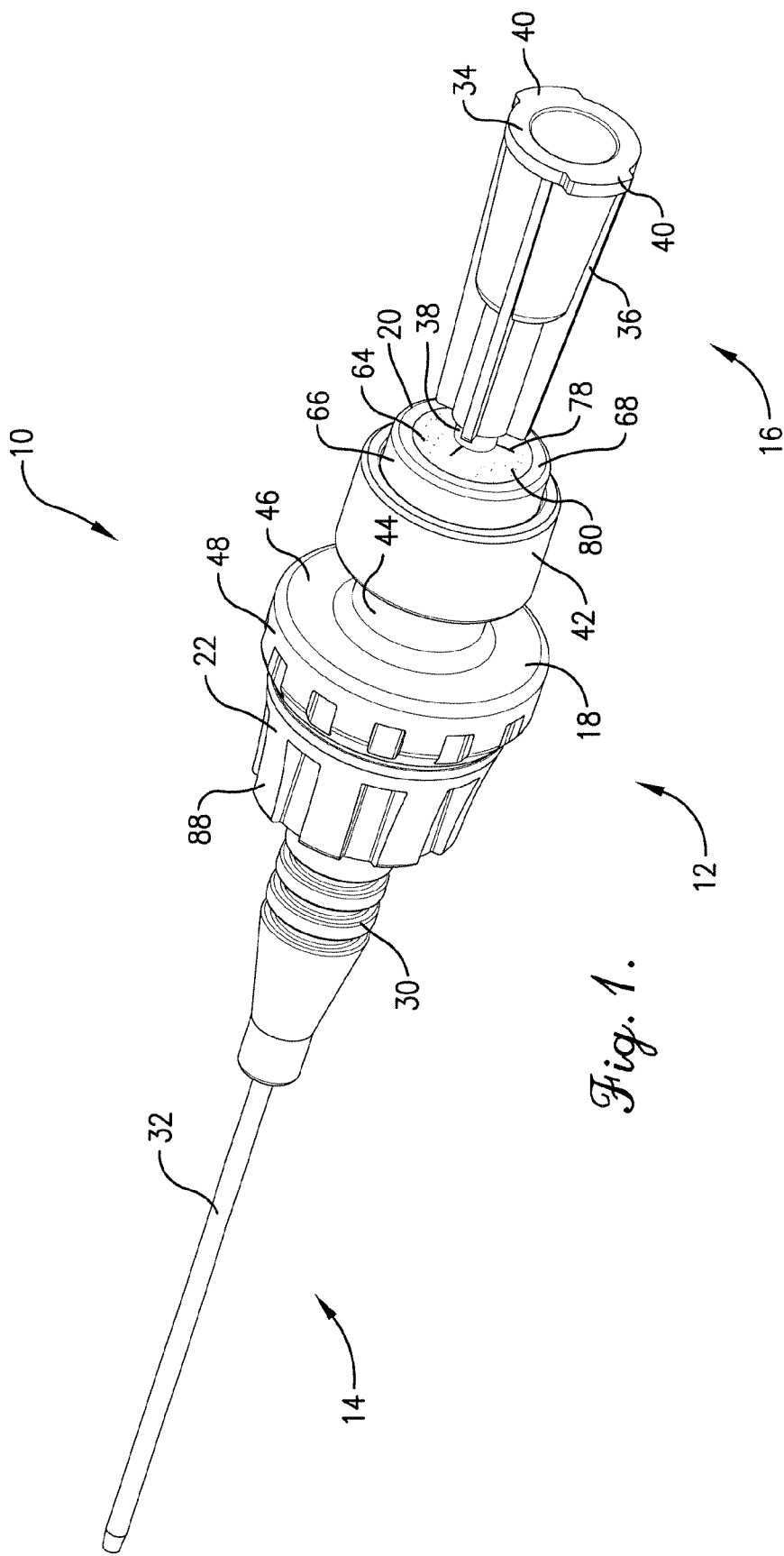
FIG. 1 is a perspective view of a catheter assembly constructed in accordance with a preferred embodiment of the present invention, with the catheter assembly including a peripheral catheter, an intravascular injection site, and a blunt cannula.

Turning to FIGS. 1, 2, and 3, a catheter assembly 10 selected for illustration generally includes an injection site 12, a peripheral catheter 14 secured to the distal end of the site 12, and a cannula 16 removably inserted into the proximal end of the injection site. The injection site 12 is constructed in accordance with a preferred embodiment of the present invention. Although the injection site 12 is shown with the peripheral catheter 14 and cannula 16, it will be appreciated that the site 12 can be used in other applications. For example, the injection site 12 could be used with a central venous catheter (CVC), another intravascular catheter, or a needle. Furthermore, the injection site 12 could be used with other types of connection components, tubing, etc. Moreover, as will be appreciated, the principles of the present invention are not limited to an injection site, but rather encompass any intravascular component utilizing the inventive valve arrangement described herein. Yet further, the illustrated catheter assembly 10 is similar in many respects to the assembly disclosed in co-pending U.S. application Ser. No. 11/277,471, filed Mar. 24, 2006, entitled INTRAVENOUS INJECTION SITE WITH SPLIT SEPTUM AND PRESSURE ACTIVATED FLOW CONTROL VALVE, which is hereby incorporated in its entirety by reference herein.

The illustrated injection site 12 preferably includes a support body 18, a proximal split septum unit 20, a distal luer lock fitting 22, and a unitary pressure-actuated flow control valve 24. Again, it will be shown that the injection site 12 could be alternatively configured with respect to the critical aspects of the present invention. As used herein, the terms "distal" and "proximal" refer, respectively, to directions toward and away from a patient.

In more detail, the illustrated peripheral catheter 14 is itself entirely conventional and includes an annular proximal base 26 with diametrically opposed connection tabs 28 for threaded connection to the fitting 22. The catheter 14 also includes a distally extending barrel 30 and cannula 32 secured to the distal end of the barrel 30. As is customary, the cannula 32 is inserted into a patient so that medicaments can be injected and fluids can be aspirated via the injection site 12. As previously mentioned, the principles of the present invention are equally applicable to other catheter designs, as well as other components permanently or removably secured to the injection site 12.

The illustrated cannula 16 is also conventional in construction and preferably includes a proximal annular base 34 and an externally ribbed barrel 36 terminating in an elongated injection lumen 38. The base 34 is preferably provided with diametrically opposed connection tabs 40 configured for threaded connection with a standard luer lock fitting. It is particularly noted that the cannula 16 is a so-called "blunt cannula," preferably formed of a relatively rigid plastic and intended to provide needleless connection with a septum. Although a needle could conceivably be used with the injection site 12, those ordinarily skilled in the art will appreciate that a split septum is typically designed for use with a blunt cannula. The illustrated cannula 16 is configured to be attached to other components for transferring fluid via the injection site 12 (in either of infusion and aspiration directions), such as tubing, a syringe, or a gravity supply fluid source.

Turning to FIGS. 4-7, the support body 18 serves to support and interconnect the septum unit 20 and luer lock fitting 22. The support body 18 preferably comprises a molded synthetic resin rigid body and includes a septum well 42, a tubular mid-section 44, and a cup-like structure that includes a valve seat 46 and a sidewall 48. The septum well 42 presents a socket for receiving the septum unit 20, and the socket is partly defined by a distal septum-engaging surface 50 and an annular interior groove 52 adjacent a proximal end of the septum well 42. As will be discussed, the surface 50 is designed to restrict distal displacement of the septum when the cannula 16 is inserted therein and, more preferably, precompress the septum prior to cannula insertion. The surface 50 projects proximally to provide the desired degree of precompression. Specifically, the surface 50 is rounded with a central apex 53, and the surface 50 preferably extends in a proximal direction at least about 0.015 of an inch (measured axially from the distalmost circumferential periphery of surface 50 to the central apex 53). More preferably, the "height" of the surface is about 0.026 of an inch. However, the principles of the present invention are equally applicable where the septum well 42 is alternatively configured or where the support body 18 is devoid of the septum well 42 (e.g., where the injection site 12 does not include the septum unit 20). It is also possible for the inventive aspects of the valve component to be used without the septum unit 20.

The mid-section 44 is integrally formed with and extends distally from the septum well 42 and presents an axially-extending proximal passageway 54. The passageway 54 extends through the central apex 53 of the septum-engaging surface 50. The preferred passageway 54 has a diameter that ranges from about 0.099 inches to about 0.112 inches. The mid-section 44 serves as the fluid connection between the septum well 42 and the cup-like structure that holds the flow control valve 24, and thereby provides a space for receiving the distal end of cannula 16 during cannula insertion (see FIG. 5). However, it is also within the scope of the present invention to have additional or alternative structure provided to interconnect the cup-like structure and septum well 42. Furthermore, the support body 18 could be devoid of the mid-section 44 so that the septum well 42 and cup-like structure are directly connected.

Turning again to FIGS. 4-7, the cup-like structure is configured to hold the flow control valve 24, as will be discussed further. The valve seat 46 comprises a radially-extending wall attached to the distal end of the mid-section 44 and presents a proximal flange-engaging face 56. The sidewall 48 comprises an annular wall that presents interior, annular, proximal and distal axial surfaces 58,60 that are joined by a shoulder 62 (see FIG. 7). The sidewall 48 extends endlessly about the valve seat 46 and is preferably integrally formed with the valve seat 46. Preferably, the illustrated surfaces 56,58,60,62 cooperatively form a socket that fluidly communicates with the passageway 54 and is configured to receive the flow control valve 24 and luer lock fitting 22. However, for some aspects of the present invention, the preferred socket could be alternatively configured to receive the luer lock fitting 22 and flow control valve 24. The sidewall 48 presents an outermost diameter of the injection site that is preferably less than about one (1) inch and, more preferably, is less than about 9/16 of an inch.

The split septum unit 20 preferably includes a resilient elastomeric septum body 64, and an annular rigid synthetic resin septum holder 66. However, the principles of the present invention are applicable where the septum unit 20 does not include the holder 66. The illustrated holder 66 has opposed, annular, proximal and distal ends 68,70, and is disposed about body 64. The outer surface of the holder 66 also has an outwardly projecting, annular detent 72. As illustrated, the outer periphery of resilient body 64 has an annular groove 74, while the inner surface of holder 66 is equipped with a mating, annular rib 76; the interfit of rib 76 into groove 74 securely fastens the holder 66 to body 64. The internal diameter of the ring-shaped septum holder 66 and the outer diameter of the septum body 64 are preferably dimensioned to closely complement one another, whereby the septum holder 66 provides little or no pre-loading of the septum body 64.

The body 64 also presents a split 78 extending fore and aft between proximal and distal faces 80,82 thereof. This allows insertion of cannula 16 through the septum unit 20, as will be described. The split 78 is preferably a tri-slit (or Y-shaped slit), although a linear split or other split configurations are entirely within the ambit of the present invention. However, those ordinarily skilled in the art will appreciate that certain principles of the present invention are not limited to the illustrated septum design. For example, the septum holder 66 is not always required or the design of the septum body 64 may be varied, such as changing the configuration of the split. Furthermore, for some aspects of the present invention, the injection site could be devoid of the septum unit 20 entirely (e.g., the site 12 may alternatively include a luer lock connection in place of the split septum).

In the illustrated embodiment, the holder 66 projects proximally from the well 42 so that the proximal terminal face 68 of the holder 66 is spaced proximally from the proximal terminal face 80 of the support body 18. Moreover, the body 64 and holder 66 are preferably configured to present a substantially coplanar proximal septum surface (cooperatively defined by faces 68 and 80). This arrangement provides a generally smooth swabable surface that greatly enhances the cleanliness of the site 12. However, it is entirely within the ambit of certain aspects of the present invention to provide the site 12 with an alternative proximal configuration. For example, the proximal surfaces of septum body 64, septum holder 66, and well 42 may be axially offset relative to one another. Furthermore, if desired, the proximal face of the well 42 could also be coplanar with the faces 68 and 80. In the preferred embodiment, the faces 68 and 80 are not coplanar until the unit 20 is received within the well 42, whereupon the septum body 64 is preloaded and deflected proximally into flush relationship with the proximal face 68 (see FIGS. 4 and 7).

The septum unit 20 is received within well 46, with the septum body 64 preferably being preloaded as previously described. Furthermore, the unit 20 is inserted into well 42 until the detent 72 is seated within groove 52, which provides further pre-compression (or at least resistance to radial deflection) of the septum body 64. Yet further, as the septum unit 20 is seated within the well 42, the outer periphery of distal face 82 of body 64 comes into firm contact with the protruding septum-engaging surface 50. Consequently, the body 64 is compressed by and assumes a shape complemental to the surface 50 (see FIGS. 4-7). Additional details and advantages concerning the preferred septum unit 24 and the interconnection between the septum well 42 and septum unit 24 are disclosed in the above-incorporated U.S. application Ser. No. 11/277,471.

Turning to FIGS. 2, 2*a*, and 4-7, the luer lock fitting 22 is preferably a unitary fitting molded from a rigid synthetic resin. The fitting 22 includes a proximal annular valve seat 84, a distal annular inner barrel 86, and a distal, annular, outer, connection wall 88. The fitting 22 also presents a proximal connection end 90 with proximal and distal axial surfaces 92,94, and proximal and distal shoulders 96,98 and is designed to be received by the distal socket of the support body 18 (see FIG. 7). The connection end 90 is designed to mate with the sidewall 48 so that respective surfaces 58,92, shoulders 62,96, and surfaces 60,94 engage one another to interconnect the fitting 22 and the support body 18 and secure the flow control valve 24, as will be discussed further. As best seen in FIG. 7, the annular base 34 of peripheral catheter 14 is threaded into the fitting 22, between the inner barrel 86 and outer connection wall 88. The fitting 22 also presents an axially-extending distal passageway 100 that extends through the inner barrel 86 and valve seat 84. While the fitting 22 is preferably configured as a luer lock fitting, the principles of the present invention are equally applicable where fitting 22 includes a different type of connector for attachment to the catheter 14 (or for attachment to other infusion/aspiration set components such as a needle or tubing).

The valve seat 84 also presents a distal annular flange-engaging face 102 spaced radially between the proximal surface 92 and the passageway 100, with the distal face 102 preferably including an endless annular groove 104 for receiving and holding the flow control valve 24 precisely between the support body 18 and fitting 22. However, it is also within the scope of the present invention where the valve seat 84 is alternatively configured to receive the flow control valve 24, as will be discussed further.

Turning to FIGS. 3, 3*a*, and 4-7, the flow control valve 24 is configured to selectively permit infusion and aspiration fluid flow through the injection site 12 and includes a peripheral flange 106 and a concavo-convex, substantially dome-shaped central body 108 surrounded by the flange 106. The body 108 and flange 106 are preferably integrally formed from resilient silicone, but could include another synthetic resin material. The body 108 preferably comprises a wall 110 that presents concave and convex surfaces 110*a*, 110*b*. The wall 110 also presents a wall apex and a thickness that decreases progressively to the apex. The body 108 also includes a rib 112 extending along the concave surface of the wall 110. Yet further, the body 108 presents opposed interior valve edges 114 that extend perpendicularly relative to the rib 112 and extend axially through the body 108 to define a slit 116 (see FIGS. 4-7). Additional preferred features of the body 108 are disclosed in U.S. patent application Ser. No. 10/304,833, filed Nov. 26, 2002, entitled PRESSURE ACTUATED FLOW CONTROL VALVE, which is hereby incorporated in its entirety by reference herein.

The flange 106 includes an endless annular flange wall 118 surrounding and attached to the body 108 (see FIG. 3*a*). The flange 106 also includes an endless annular valve-seating projection 120 extending distally from the flange wall 118 and spaced radially between an outermost edge 122 of the flange wall 118 and the body 108. Preferably, the projection 120 is spaced radially outwardly from the body 108 to permit the edges 114 to flex between open infusion and aspiration configurations, as will be discussed. The principles of the present invention are also applicable where the projection 120 is alternatively configured to provide a mechanism for precisely seating the flow control valve 24 within the injection site 12. For instance, the projection could extend proximally from the flange wall 118. Furthermore, multiple projections 120 could extend distally and/or proximally from the flange wall 118 to secure the flow control valve 24. For example, the projection 120 could comprise multiple arcuate segments that are spaced circumferentially from one another and cooperatively extend about the body 108. Alternatively, the projection 120 could include multiple radially-spaced segments.

The flow control valve 24 is assembled between the support body 18 and fitting 22 by positioning the valve 24 on valve seat 84. In particular, the apex of the valve 24 is inserted into a proximal end of the passageway 100, and the projection 120 is inserted into the annular groove 104. The projection 120 and groove 104 are preferably shaped to guide the flow control valve 24 into axial alignment with the fitting 22. Preferably, the groove 104 and projection 120 are complementally shaped so that the projection 120 fits snugly within the groove 104 and the flow control valve 24 is coaxially aligned with the fitting 22 (thereby positioning the dome-shaped central body 108 concentrically within the passageway 100). In this manner, the interengagement between the groove 104 and projection 120 restricts relative radial movement between the flow control valve 24, support body 18, and fitting 22. In addition, the groove 104 and projection 120 permit the flow control valve 24 to be selectively angularly rotated about the valve axis and relative to the support body 18 and fitting 22, although this is likely unnecessary with the illustrated embodiment because of the symmetrical construction of the control valve 24.

The illustrated configuration of groove 104 and projection 120 is preferred for axially aligning the flow control valve 24 within the injection site 12. However, it is also within the ambit of the present invention where the valve seat 84 presents an alternative opening to receive the projection 120 and thereby axially (and perhaps rotationally) align the flow control valve 24. For instance, the valve seat 84 could present multiple openings to receive complemental projecting segments. It is also within the ambit of the present invention where the projection 120 extends proximally from flange wall 118 and is received by a groove in valve seat 46. Furthermore, both valve seats 46,84 could include grooves for receiving complemental oppositely extending projections of the flow control valve 24.

The flow control valve 24 is also positioned onto the valve seat 46 by locating a proximal surface of the flange wall 118 against the flange-engaging face 56. As discussed previously, the fitting 22 is secured to the support body 18 by inserting the connection end 90 into the distal socket of the support body 18. The support body 18 and fitting 22 are further secured by attaching respective adjacent pairs of surfaces using a conventional ultrasonic welding process to form an hermetic seal between the support body 18 and fitting 22. The principles of the present invention are also applicable where the support body 18 and fitting 22 are alternatively attached to one another, e.g., where the support body 18 and fitting 22 are attached by a snap-fit interengagement or adhered to one another using a suitable adhesive.

With the connection end 90 inserted, the support body 18 and fitting 22 cooperatively present an internal valve chamber that receives the flow control valve 24. The faces 56,102 engage the flange wall 118 on corresponding sides and compress the flange wall 118 into a compressed state so as to firmly hold the valve 24 within the injection site 12. More preferably, the support body 18 and fitting 22 are interconnected so that a thickness dimension T (see FIG. 3a) of the flange wall 118 is axially compressed from an uncompressed state to the compressed state by an amount that ranges from about 0.003 inches to about 0.008 inches. Most preferably, the amount of compression of the thickness dimension T between uncompressed and compressed states is about 0.005 inches.

The flange wall 118 also presents an outermost diameter D1 that preferably ranges from about 0.341 inches to about 0.355 inches. Also, the outermost diameter D1 is preferably less than an outermost chamber diameter D2 (see FIG. 7). More preferably, the outermost diameter D1 ranges from about 0.010 inches to about 0.030 inches smaller than the chamber diameter D2 when the flange wall 118 is in the uncompressed state. Most preferably, the outermost diameter D1 is about 0.020 inches smaller than chamber diameter D2. This configuration provides a slight clearance between the flange wall 118 and support body 18. As a result, the illustrated flow control valve 24 can be precisely coaxially aligned with the support body 18, fitting 22, and passageways 54,100, and the flange wall 116 can be compressed between the support body 18 and fitting 22 while permitting the central body 108 to flex normally to allow aspiration and infusion flow. In particular, it has been found that this "loose fit" between the installed flow control valve 24 and axial surface 58 allows the projection 120 to align the flow control valve 24 to the valve seat 84 and restricts inadvertent off-axis positioning of the valve 24 relative to the support body 18 and fitting 22. Furthermore, the loose fit between the outermost edge 122 and axial surface 58 promotes normal opening of the slit 116 for injection and aspiration flow, with inadvertent or premature opening of the slit being restricted. Thus, the illustrated injection site 12 is designed to minimize valve failures, particularly those that result from injection site manufacturing and assembly.

Turning to FIGS. 4 and 6, the valve 24 is preferably designed to selectively prevent fluid flow in the proximal direction (corresponding to aspiration flow through the injection site 12). More particularly, the valve 24 prevents proximal flow when an aspiration pressure differential (i.e., where the pressure against the convex surface 110b of the wall 110 is greater than the pressure against the concave surface 110a of the wall 110) across the valve 24 is below a set aspiration amount (see FIG. 4). The set aspiration amount is generally greater than the venous pressure (relative to atmospheric pressure) of the patient when fluid is not being injected or aspirated through the injection site 12. That is to say, when the valve 24 experiences the typical venous pressure of the patient, the corresponding aspiration pressure differential is less than the set aspiration amount and is not sufficient to open the valve 24 (i.e., the edges 114 are in sealing engagement with each other in the closed configuration). However, when it is desired to aspirate fluid across the valve 24, fluid can be drawn through the injection site 12 by reducing the fluid pressure on a proximal side of the valve 24 (e.g., by drawing fluid with a syringe) so that the aspiration pressure differential exceeds the set aspiration amount. This causes the valve 24 to open (i.e., as edges 114 shift proximally and away from each other into the open aspiration configuration) and allow aspiration flow through passageways 54,100 (see FIG. 6).

Turning to FIGS. 4 and 5, the valve 24 is also preferably designed to selectively prevent fluid flow in the distal direction (corresponding to infusion through the injection site 12) when the valve is in the closed configuration. The valve 24 prevents distal flow when an infusion pressure differential (i.e., where the pressure against the concave surface 110a of the wall 110 is greater than the pressure against the convex surface 110b of the wall 110) across the valve 24 is below a set infusion amount. When an external pressure is applied to a proximal side of the valve 24 (e.g., by injecting fluid from a syringe or other fluid supply) and the infusion pressure differential exceeds the set infusion amount, the valve 24 opens into the open infusion configuration (where the edges 114 are shifted distally and away from each other) to allow infusion flow through passageways 54,100 (see FIG. 5). It is also noted that the valve 24 is preferably configured so that the set aspiration pressure differential required to open the valve 24 is greater than the set infusion pressure differential required to open the valve 24.

In operation, the injection site 12 permits infusion flow from the cannula 16 to the peripheral catheter 14 when the infusion pressure differential exceeds the set infusion amount. During infusion, the interior valve edges 114 are shifted in the distal direction and at least partly away from each other to open the slit 116 and allow infusion flow to pass from the proximal passageway 54 to the distal passageway 100 (see FIG. 5). Similarly, the injection site 12 permits aspiration flow from the catheter 14 to the cannula 16 when the aspiration pressure differential exceeds the set aspiration amount. During aspiration, the interior valve edges 114 are shifted in the proximal direction and at least partly away from each other to open the slit 116 and allow aspiration flow to pass from the distal passageway 100 to the proximal passageway 54 (see FIG. 6).

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An intravascular valve component comprising:
   a valve case including attached proximal and distal case portions,
   said case portions presenting respective spaced apart fluid ports and a fluid passageway extending between the ports; and
   a flexible pressure-actuated flow control valve disposed along the fluid passageway to control fluid flow therethrough,
   said valve including a generally dome-shaped central valve wall having a slit at a general apex of the dome and an annular flange surrounding the central valve wall,
   said annular flange including a radially-extending flange wall having a radially outermost edge and a valve-seating projection extending axially from the flange wall and spaced radially outwardly from said valve wall and between said outermost edge and the valve wall to permit said slit to flex between open infusion and aspiration configurations,
   one of said case portions presenting an opening,
   said opening presenting a generally arcuate-shaped groove having a tapered inner surface,
   said projection being generally arcuate-shaped and having a tapered outer surface,
   said flange wall being engagingly received between the attached case portions,
   wherein said tapered inner surface of the groove and said tapered outer surface of the projection are complementally shaped such that the projection is received within the groove and engages the groove to substantially restrict radial movement of the flow control valve relative to the valve case and to coaxially align the valve with the one of said case portions presenting said opening to thereby position the valve wall concentrically within the fluid passageway.

2. The intravascular valve component as claimed in claim 1,
   said case portions presenting respective generally planar proximal and distal flange-receiving surfaces opposed to one another,
   said flange wall presenting generally planar proximal and distal surfaces respectively received between said proximal and distal flange-receiving surfaces of said case portions, such that said proximal and distal surfaces of said flange wall respectively contact a majority of an area of said proximal and distal flange-receiving surfaces to compress the flange wall of the flow control valve therebetween.

3. The intravascular valve component as claimed in claim 2,
   said flange wall comprising an endless annular wall presenting said radially outermost edge,
   said case portions cooperatively presenting a valve chamber that receives the annular flange,
   said valve chamber being partly defined by a radially outermost internal surface extending axially between the opposed flange-receiving surfaces and presenting an outermost chamber diameter dimension,
   said radially outermost edge having an axially-extending thickness and an uncompressed flange diameter dimension,
   wherein said uncompressed flange diameter dimension along said edge is less than the outermost chamber diameter dimension, such that the valve chamber permits radial expansion of the flange wall as the flange wall is compressed between the flange-receiving surfaces,
   wherein a distance between said radially outermost edge of said uncompressed flange and said radially outermost internal surface of said valve chamber is substantially the same at a majority of points along said thickness of the outermost edge of the flange.

4. The intravascular valve component as claimed in claim 3,
   said uncompressed flange diameter dimension being about 0.020 inches less than the chamber diameter dimension.

5. The intravascular valve component as claimed in claim 2,
   said valve wall presenting proximal and distal valve surfaces, said slit being normally closed and extending between the proximal and distal valve surfaces,
   said valve wall flexing to open the slit in response to an infusion fluid pressure differential across the wall, wherein the pressure against the proximal valve surface is greater than the pressure against the distal valve surface,
   said valve wall flexing to open the slit in response to an aspiration fluid pressure differential across the wall, wherein the pressure against the distal valve surface is greater than the pressure against the proximal valve surface.

6. The intravascular valve component as claimed in claim 5,
   said dome-shaped valve wall comprising a concavo-convex wall that projects distally from the flange wall, with the proximal valve surface being concave and the distal valve surface being convex.

7. The intravascular valve component as claimed in claim 6,
   said projection extending distally from the flange wall.

8. The intravascular valve component as claimed in claim 6,
   said projection extending proximally from the flange wall.

9. The intravascular valve component as claimed in claim 1, wherein said projection engages the groove along said tapered outer surface of the projection.

* * * * *